US008922643B2

(12) United States Patent
Ji et al.

(10) Patent No.: US 8,922,643 B2
(45) Date of Patent: Dec. 30, 2014

(54) APPARATUS FOR INSPECTING LIGHT EMITTING DIODE AND INSPECTING METHOD USING SAID APPARATUS

(75) Inventors: Won Soo Ji, Suwon-si (KR); Oh Seok Kwon, Hwaseong-si (KR); Choo Ho Kim, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 506 days.

(21) Appl. No.: 13/412,197

(22) Filed: Mar. 5, 2012

(65) Prior Publication Data

US 2012/0249779 A1     Oct. 4, 2012

(30) Foreign Application Priority Data

Mar. 28, 2011   (KR) .................. 10-2011-0027761

(51) Int. Cl.
*H04N 7/18*     (2006.01)
*G01N 21/00*    (2006.01)
*G01N 21/88*    (2006.01)
*G01N 21/956*   (2006.01)

(52) U.S. Cl.
CPC .......... *G01N 21/8806* (2013.01); *G01N 21/956* (2013.01); *G01N 2021/8845* (2013.01)
USPC .......... 348/131; 382/141; 356/237.1

(58) Field of Classification Search
CPC .......... G01N 21/8806; G01N 21/95684; G01N 21/88; G01N 21/9501; G01N 21/94; G01N 21/956; H04N 5/2354; H04N 7/18; G06T 7/0004; G06T 2207/30148; G06T 2207/30164; G06T 7/0006
USPC .......... 348/131; 382/141
See application file for complete search history.

(56) References Cited

U.S. PATENT DOCUMENTS

| 2004/0076739 A1 | 4/2004 | Yokono et al. |
| 2009/0136120 A1 | 5/2009 | Onushkin et al. |
| 2009/0201577 A1 | 8/2009 | LaPlante et al. |
| 2010/0246936 A1* | 9/2010 | Ji et al. .......... 382/149 |

FOREIGN PATENT DOCUMENTS

| CN | 101552313 A | 10/2009 |
| CN | 101828139 A | 9/2010 |
| JP | 10-38541 A | 2/1998 |
| JP | 2005-049308 A | 2/2005 |

(Continued)

OTHER PUBLICATIONS

Communication dated Dec. 4, 2013 issued by the State Intellectual Property Office of P.R. China in counterpart Chinese Patent Application No. 201210086528.6.
Communication dated Jun. 25, 2013, issued by the Japanese Patent Office in counterpart Japanese Application No. 2012-069438.
Communication dated Oct. 1, 2014 issued by the Taiwanese Intellectual Property Office in counterpart Taiwanese Application No. 101106483.

*Primary Examiner* — Dave Czekaj
*Assistant Examiner* — Tsion B Owens
(74) *Attorney, Agent, or Firm* — Sughrue Mion, PLLC

(57) ABSTRACT

A light emitting diode (LED) inspection apparatus includes at least one LED including a phosphor applied on an emission surface, a first lighting unit to emit visible light to the LED, a second lighting unit to emit ultraviolet (UV) light to the LED, a photographing unit to generate at least one first image data by photographing the visible light reflected from the LED and to generate at least one second image data by photographing the UV light reflected from the LED, and a determination unit to determine a defect in appearance and emission characteristics of the LED using the at least one first image data and second image data.

15 Claims, 12 Drawing Sheets

(56) References Cited

FOREIGN PATENT DOCUMENTS

| | | |
|---|---|---|
| JP | 2006-162427 A | 6/2006 |
| JP | 2007-299788 A | 11/2007 |
| JP | 2009-158903 A | 7/2009 |
| JP | 2009-175150 A | 8/2009 |
| KR | 10-2009-0126610 A | 12/2009 |
| KR | 10-2010-0063851 A | 6/2010 |
| KR | 10-0990641 A | 10/2010 |
| TW | 200806777 A | 2/2008 |
| TW | 201110406 A1 | 3/2011 |
| WO | 2009/015209 A1 | 1/2009 |

\* cited by examiner

APPARATUS FOR INSPECTING LIGHT EMITTING DIODE AND INSPECTING METHOD USING SAID APPARATUS

CROSS-REFERENCE TO RELATED APPLICATION

This application claims the benefit of Korean Patent Application No. 10-2011-0027761, filed on Mar. 28, 2011, in the Korean Intellectual Property Office, the disclosure of which is incorporated herein by reference.

BACKGROUND

1. Field of the Invention

The present invention relates to an inspection apparatus for a light emitting diode (LED) and an inspection method using the same, and more particularly, to an inspection apparatus for determining inferiority of an LED by inspecting appearance and emission characteristics of the LED and an inspection method using the same.

2. Description of the Related Art

At first, a light emitting diode (LED) package had primarily been used for signaling. Recently, the LED package is applied more widely, for example, to lighting devices and a light source of a backlight unit (BLU) of a mobile phone or of a large-area display device such as a liquid crystal display (LCD). A demand for the LED is increasing since it has a relatively low power consumption and long lifespan compared to general bulbs or fluorescent lamps. As the demand increases, production of the LED is rapidly increasing. Consequently, a rate of defects occurring in the LED is also increasing. Therefore, prior to the LED being distributed to consumers, an inspection of an appearance and emission characteristics, so called photo luminescence (PL) characteristics, of the LED is performed.

A vision inspection using the naked eye or using an apparatus has been performed to prevent distribution of an LED having various external defects such as an external damage, contamination, and the like, to consumers. However, since the emission characteristics cannot be inspected by the vision inspection, a dedicated inspection for the emission characteristics is necessary.

An inspection of the emission characteristics may be performed by a microscope including an ultraviolet (UV) lamp. Here, the microscope controls light being emitted from the UV lamp, by mechanically adjusting a shutter. However, use of the mechanical shutter operation may hinder high-speed inspection of the emission characteristics. In addition, the lifespan of the apparatus may be reduced while the UV lamp increases initial expenses and maintenance expenses.

SUMMARY

An aspect of the present invention provides an inspection apparatus for reducing inspection costs and enabling high speed inspection, by determining defects of an LED regarding appearance and emission characteristics, simultaneously, and an inspection method using the same.

According to an aspect of the present invention, there is provided a light emitting diode (LED) inspection apparatus including at least one LED including a phosphor applied on an emission surface, a first lighting unit to emit visible light to the LED, a second lighting unit to emit ultraviolet (UV) light to the LED, a photographing unit to generate at least one first image data by photographing the visible light reflected from the LED and to generate at least one second image data by photographing the UV light reflected from the LED, and a determination unit to determine a defect in appearance and emission characteristics of the LED using the at least one first image data and second image data.

The LED inspection apparatus may further include a beam splitting unit to reflect the emitted visible light and transmit the reflected visible light to the LED, and to provide the visible light reflected from the LED to the photographing unit by transmitting the visible light.

The UV light reflected from the LED may include a wavelength-converted light of which a wavelength is converted by the LED and the phosphor.

The LED inspection apparatus may further include a color filter disposed at an upper portion of the LED to pass the wavelength-converted light which is included in the UV light reflected from the LED and to filter the UV light.

The photographing unit may generate second image data by photographing the wavelength-converted light passed through the color filter.

The determination unit may detect an alignment state of the LED from the first image data and determine an existence of a diode according to the alignment state.

The determination unit may compare the first image data with first reference image data when the diode is determined to exist, and determine that the LED has a defective appearance when the first image data is different from the first reference image data.

The determination unit may divide the second image data into a plurality of sections and calculate a mean value of pixels included in the plurality of sections when the LED is determined to have a normal appearance, and determine that the LED has defective emission characteristics when the mean value is beyond a tolerance range.

The determination unit may image-process the second image data when the mean value is within the tolerance range, and compare the second image data with second reference image data and determines that the LED has defective emission characteristics when the second image data is different from the second reference image data.

The LED inspection apparatus may further include a display unit to display the first image data and the second image data generated by the photographing unit, and a storage unit to map the first image data and the second image data with a result of the determination by the determination unit related to the defect in appearance and emission characteristics, and store the mapping result.

According to another aspect of the present invention, there is provided an LED inspection method including emitting visible light to at least one LED which includes a phosphor applied on an emission surface, generating at least one first image data by photographing the visible light reflected from the LED, emitting ultraviolet (UV) light to the LED, generating at least one second image data by photographing the UV light reflected from the LED, and determining a defect in appearance and emission characteristics of the LED using the first image data and the second image data.

The UV light reflected from the LED may include a wavelength-converted light of which a wavelength is converted by the LED and the phosphor.

The generating of the second image data may include passing the wavelength-converted light which is included in the UV light reflected from the LED and filtering the UV light, and generating the second image data by photographing the filtered wavelength-converted light.

The determining of the defect may include detecting an alignment state of the LED from the first image data and determining an existence of a diode according to the alignment state, comparing the first image data with first reference image data when the diode is determined to exist, and determining that the LED has a defective appearance when the first image data is different from the first reference image data.

The determining of the defect may include dividing the second image data into a plurality of sections and calculating a mean value of pixels included in the plurality of sections when the LED is determined to have a normal appearance, and determining that the LED has defective emission characteristics when the mean value is beyond a tolerance range.

The determining of the defect may include image-processing the second image data when the mean value is within the tolerance range, and comparing the second image data with second reference image data and determining that the LED has defective emission characteristics when the second image data is different from the second reference image data.

The LED inspection method may further include displaying the first image data and the second image data, and mapping the first image data and the second image data with a result of the determination related to defects in appearance and emission characteristics and storing the mapping result.

BRIEF DESCRIPTION OF THE DRAWINGS

These and/or other aspects, features, and advantages of the invention will become apparent and more readily appreciated from the following description of exemplary embodiments, taken in conjunction with the accompanying drawings of which.

DETAILED DESCRIPTION

Figure 1:
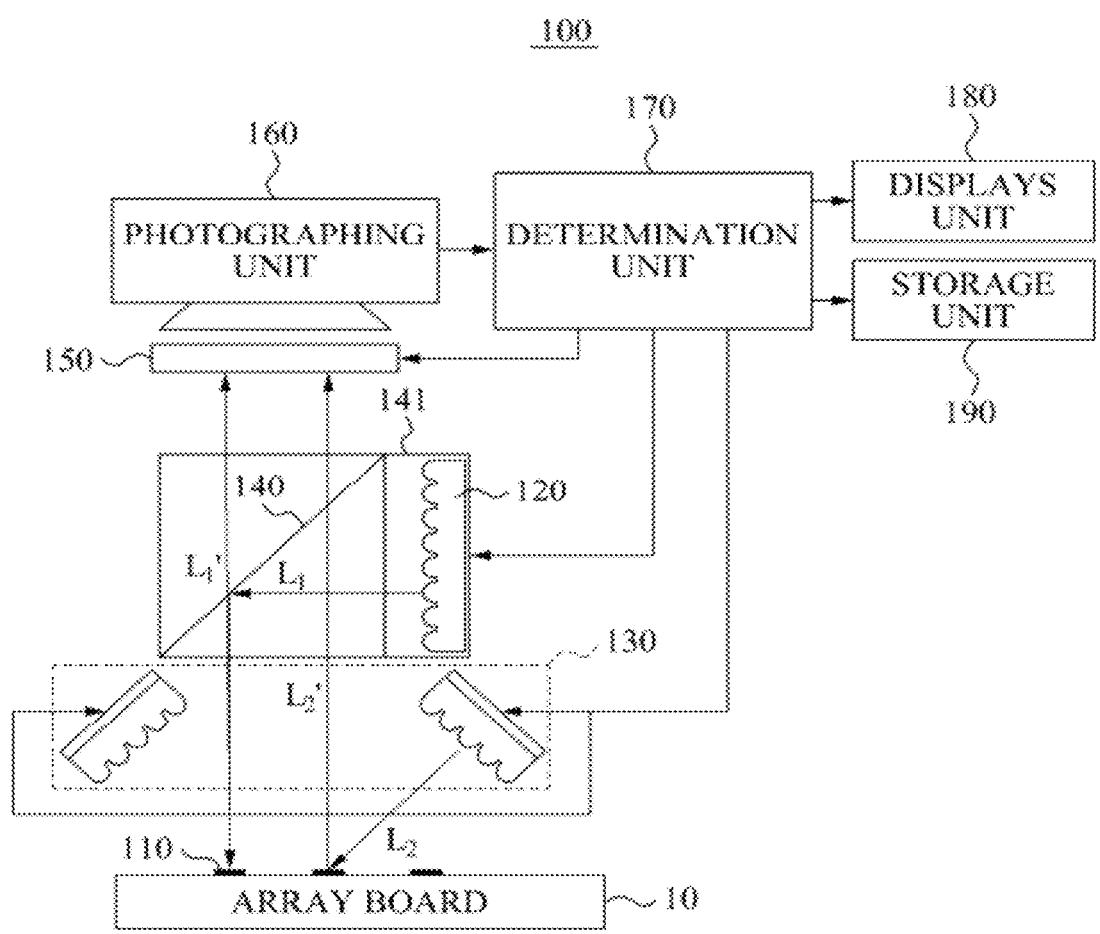
FIG. 1 is a block diagram illustrating a structure of a light emitting diode (LED) inspection apparatus according to an embodiment of the present invention.

Reference will now be made in detail to exemplary embodiments of the present invention, examples of which are illustrated in the accompanying drawings, wherein like reference numerals refer to the like elements throughout. In the following description, when it is determined that a detailed description of well-known functions related to the present invention and the construction thereof would make the gist of the present invention obscure, they will be omitted. The terminology used herein is for the purpose of describing particular embodiments only and the definition may be varied according to the intention of a user, an operator, or customs. Therefore, the terms and words should be defined based on a description of this specification.

FIG. 1 is a block diagram illustrating a structure of a light emitting diode (LED) inspection apparatus according to an embodiment of the present invention. Referring to FIG. 1, the LED inspection apparatus 100 may include an LED 110, a first lighting unit 120, a second lighting unit 130, a beam splitting unit 140, a color filter 150, a photographing unit 160, and a determination unit 170.

The LED 110 may have a chip structure including a phosphor or may have a wafer level structure. Also, the LED 110 may be in a package structure mounted on a package substrate (not shown) or in a module structure.

A plurality of the LEDs 110 may be arranged on an array board 10.

The phosphor may be applied on an emission surface of the LED 110 to convert a wavelength of light generated from the LED 110. Types of the phosphor may be varied according to a color of the light generated from the LED 110 and a color of light to be implemented using the LED 110 and the phosphor.

For example, when blue light is generated by the LED 110 and white light is to be implemented using the LED 110 and the phosphor, yellow phosphor may be used as the phosphor.

When ultraviolet (UV) light is generated by the LED 110 while white light is to be implemented using the LED 110 and the phosphor, blue, green, and red phosphors may be used as the phosphor.

The first lighting unit 120 emits a visible light $L_1$ to the LED 110. The visible light $L_1$ emitted from the first lighting unit 120 is reflected from the LED 110. The first lighting unit 120 may be a coaxial light. The coaxial light may further emit a UV light in addition to the visible light $L_1$.

The second lighting unit 130 may emit a UV light $L_2$ to the LED 110. The UV light $L_2$ emitted from the second light 130 may be reflected from the LED 110. A reflected UV light $L_2'$ may include wavelength-converted light of which a wavelength is converted by an active layer and a phosphor of the LED 110. That is, the active layer of the LED 110 receiving the UV light $L_2$ may be excited by the UV light $L_2$, thereby generating light having a wavelength corresponding to a material of the active layer. Accordingly, a wavelength of the UV light $L_2$ is converted by the phosphor.

The second lighting unit 130, in opposition to the operation of the first lighting unit 120, may be turned on and off. For example, when the first lighting unit 120 is turned on, the second lighting unit 130 may be turned off. Further, when the first lighting unit 120 is turned off, the second lighting unit 130 may be turned on.

The second lighting unit 130 may be a vertical light and include a plurality of vertical lighting units. The vertical light may further emit visible light in addition to the UV light $L_2$. That is, the vertical light may emit the UV light $L_2$ and the visible light, separately.

The beam splitter 140 may be disposed at an upper portion of the array board 10. By reflecting the visible light $L_1$ emitted from the first lighting unit 120, the beam splitter 140 may emit the visible light $L_1$ to the LED 110 disposed on the array board 10. The beam splitter 140 may be disposed in a support body 141.

In addition, the beam splitter 140 may transmit a visible light $L_1'$ reflected from the LED 110. More specifically, the visible light $L_1$ emitted from the first lighting unit 120 is reflected by the beam splitter 140, thereby being transferred to the LED 110. The visible light $L_1$ is reflected from the LED 110 and becomes the visible light $L_1'$ as transmitted by the beam splitter 140.

The color filter 150 may transmit the visible light $L_1'$ and the UV light $L_2'$ reflected from the LED 110. During this, the color filter 150 may remove UV components from the visible light $L_1'$ and the UV light $L_2'$, thereby preventing the UV components from advancing to the photographing unit 160.

In addition to the UV light $L_2$ emitted from the second lighting unit 120, the UV light $L_2'$ reflected from the LED 110 may further include wavelength-converted light of which a wavelength is converted by the active layer and the phosphor of the LED 110. Thus, the color filter 150 may transmit the wavelength-converted light included in the UV light $L_2'$ while selectively removing only the UV light $L_2$ so that the UV components are prevented from advancing to the photographing unit 160.

The color filter 150 may be fixed to the upper portion of the array board 10 on which the LED 110 is disposed. However, the color filter 150 may be movable. For example, the color filter 150 may be disposed at the upper portion of the array board 10 when the second lighting unit 130 is on, and may be moved to another position when the second lighting unit 130 is off.

The photographing unit 160 may generate at least one first image data by photographing the visible light $L_1'$ reflected from the LED 110. Also, the photographing unit 160 may generate at least one second image data by photographing the UV light $L_2'$ reflected from the LED 110 and passed through the color filter 150. The photographing unit 160 may be a photographing device including a charge coupled device (CCD) camera.

The determination unit 170 may determine a defect in appearance and emission characteristics of the LED 110 using the first image data and the second image data. According to an exemplary embodiment, the determination unit 170 may determine whether the LED 110 has a defective appearance using the first image data and determine whether the LED 110 has defective emission characteristics using the second image data.

The determination unit 170 may detect an alignment state of the LED 110 from the first image data. The determination unit 170 may determine an existence of a diode according to the detected alignment state.

The determination unit 170 may check the alignment state detected from the first image data, and determine that the diode is absent when the alignment state has a discontinuous section or an undetectable section. With respect to the diode-absent section, an inspection of the defect in the appearance and the emission characteristics of the LED 110 is not performed.

When the first image data includes the diode, the determination unit 170 may compare the first image data with first reference image data and thereby determine the defect of the appearance of the LED 110.

The first reference image data may be image data photographed by emitting a visible light to a standard LED corresponding to a model or specifications. That is, the first reference image data may be reference data corresponding to a normal state. For example, the first reference image data may be an image photographed by emitting the visible light to the standard LED having the same model and specifications as the LED 110.

According to an embodiment of the present invention, the determination unit 170 may detect a border from the first image data and compare the detected border with a reference border of the first reference image data, thereby determining a defect in the appearance of the LED 110. When the border detected from the first image data is identical to the reference border of the first reference image data, the determination unit 170 may determine that the LED 110 has a normal appearance.

Conversely, when the border detected from the first image data is different from the reference border, the determination unit 170 may determine that the LED 110 has a defective appearance. For example, the LED 110 may have damage such as breakage or may be contaminated.

According to another embodiment of the present invention, the determination unit 170 may measure pixel values of respective pixels constituting the first image data and compare the measured pixel values with reference pixel values corresponding to the respective pixels of the first image data, thereby determining a defect in the appearance of the LED 110. When a pixel value of an m-row, n-column pixel included in the first image data is equal to a reference pixel value of an m-row, n-column pixel included in the first reference image data, the determination unit 170 may determine that the LED 110 has a normal appearance.

However, when the pixel value of the m-row, n-column pixel included in the first image data is different from a reference pixel value of the m-row, n-column pixel included in the first reference image data, the determination unit 170 may determine that the LED 110 has a defective appearance. For example, the LED 110 may have damage such as breakage or may be contaminated.

When the LED 110 is determined to have a normal appearance, the determination unit 170 may determine a defect in the emission characteristics of the LED 110 using the second image data.

The determination unit 170 may divide the second image data into a plurality of areas, for example diode unit areas, and calculate a mean value of pixels included in the plurality of areas. The second image data may be an image of the wavelength-converted light filtered by the color filter out of the UV light $L_2'$ reflected from the LED 110. Therefore, the second image data may be an image that includes pixel values corresponding to light generated from the active layer excited by the UV light and light which is wavelength-converted by the phosphor.

For example, when the active layer is excited by the UV light, thereby generating blue light, while the phosphor converts the UV light to yellow light, the pixels included in the plurality of areas may have a pixel value corresponding to mixture of the blue light and the yellow light. Therefore, when the LED 110 has normal emission characteristics, the mean value of the pixels in each area may be within a tolerance range. Here, the tolerance range may be varied according to a model and specifications of the LED 110 and the phosphor.

When the mean value calculated from the plurality of areas is within the tolerance range, the determination unit 170 may image-process the second image data and compare the second image data with second reference image data, thereby determining a defect in the emission characteristics of the LED 110.

As aforementioned, the second image data may be an image that includes the light generated from the active layer excited by the UV light and the light which is wavelength-converted by the phosphor. Due to the pixel value corresponding to the wavelength-converted light, a minor dot or spot may not be accurately inspected in the second image data. Therefore, the determination unit 170 may image-process the second image data into a black-and-white image.

The determination unit 170 may compare the image-processed second image data with the second reference image data. When the image-process second image data is identical to the second reference image data, the determination unit 170 may determine that the LED 110 has normal emission characteristics. When the second image data is different from the second reference image data, the determination unit 170 may determine that the LED 110 has defective emission characteristics.

The determination unit 170 may determine the defect in the emission characteristics of the LED 110 by comparing the pixels included in the image-processed second image data with the pixels included in the second reference image data one by one.

The second reference image data may be image data photographed by emitting UV light to a standard LED that includes a phosphor, corresponding to a model or specifications. That is, the second reference image data may be reference data corresponding to a normal state. For example, the second reference image data may be an image photographed by emitting UV light to the standard LED having the same model and specifications as the LED 110.

The LED inspection apparatus 100 may further include a display unit 180 and a storage unit 190.

The display unit 180 may display the first image data and the second image data generated by the photographing unit 160. Therefore, an operator may inspect the appearance and the emission characteristics of the LED by naked eyes through the display unit 180.

When the defect is determined by the determination unit 170, the storage unit 190 may map the determination result with the first image data and the second image data and store the mapping result.

That is, the LED inspection apparatus 100 may be input with the model and the specification of the LED 110 prior to the inspection. The storage unit 190 may map the input model and specifications, the first image data and the second image data related to the LED 110, and the determination result such as "defective" or "normal", and then store the mapping result data.

The LED inspection apparatus 100 shown in FIG. 1 may determine the defect by inspecting the appearance and the emission characteristics of the LED 110, simultaneously, accordingly simplifying the inspection process. In addition, using the second lighting unit 130 which emits the UV light as an inspection light source, the LED inspection apparatus 100 may perform the inspection at a high speed.

Although, with reference to FIG. 1, the determination unit 170 has been illustrated to determine the defect of the LED by pattern matching using the first reference image data and the second reference image data, the present invention is not limited to the embodiment. For example, the determination unit 170 may use a defective shape recognition method or an image processing method.

Figure 2:
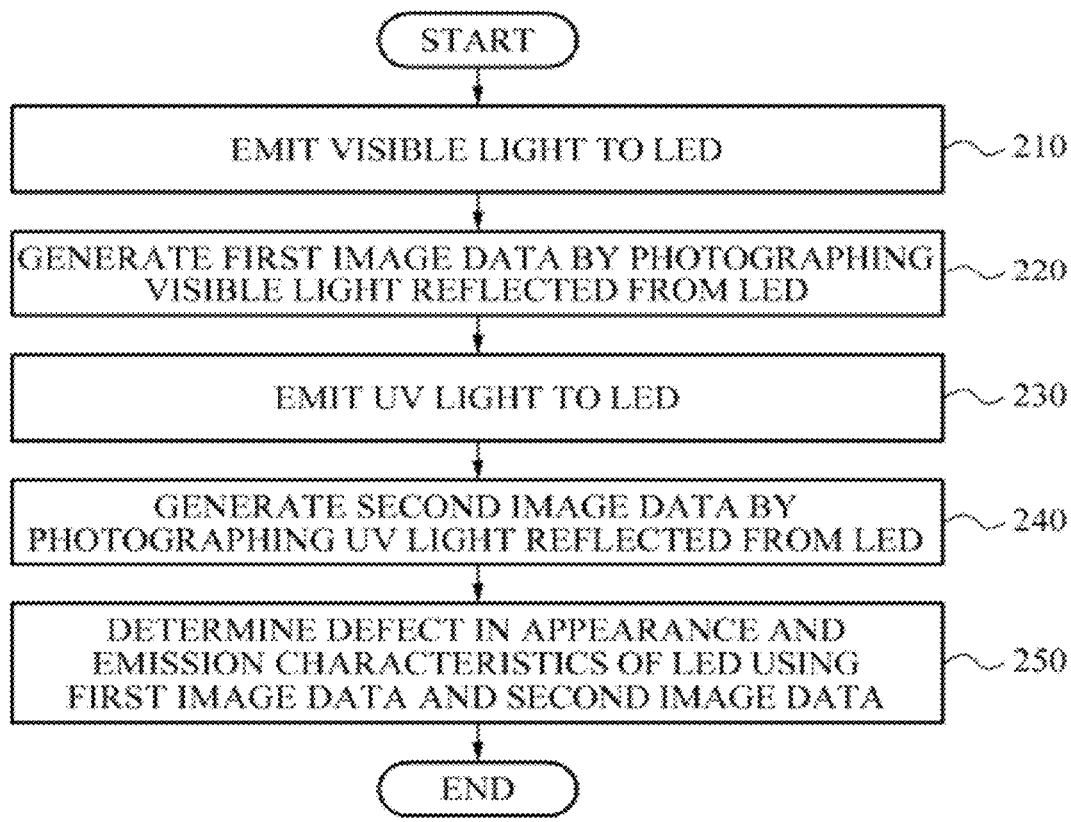
FIG. 2 is a flowchart illustrating an LED inspection method according to an embodiment of the present invention.

FIG. 2 is a flowchart illustrating an LED inspection method according to an embodiment of the present invention. The LED inspection method may be performed by the LED inspection apparatus 100 shown in FIG. 1.

Referring to FIG. 2, the LED inspection apparatus 100 may turn the first lighting unit 120 on to emit the visible light $L_1$ to the LED 110, in operation 210. At least one LED 110 may be arranged on the array board 10. The LED 110 may include a phosphor applied on an emission surface.

In operation 220, the LED inspection apparatus 100 may generate the first image data by photographing the visible light $L_1'$ reflected from the LED 110.

In operation 230, the LED inspection apparatus 100 may turn the second lighting unit 130 on to emit the UV light $L_2$ to the LED 110. When the second lighting unit 130 is turned on, the first lighting unit 120 may be turned off. Also, when the second lighting unit 130 is turned on, the color filter 150 may be moved to the upper portion of the LED 110 disposed on the array board 10.

In operation 240, the LED inspection apparatus 100 may image the UV light $L_2'$ reflected from the LED 110, thereby generating the second image data. In this instance, the UV light $L_2'$ may have UV components removed by the color filter 150.

In operation 250, the LED inspection apparatus 100 may determine the defect in the appearance and the emission characteristics of the LED 110 using the first image data and the second image data.

Figure 3:
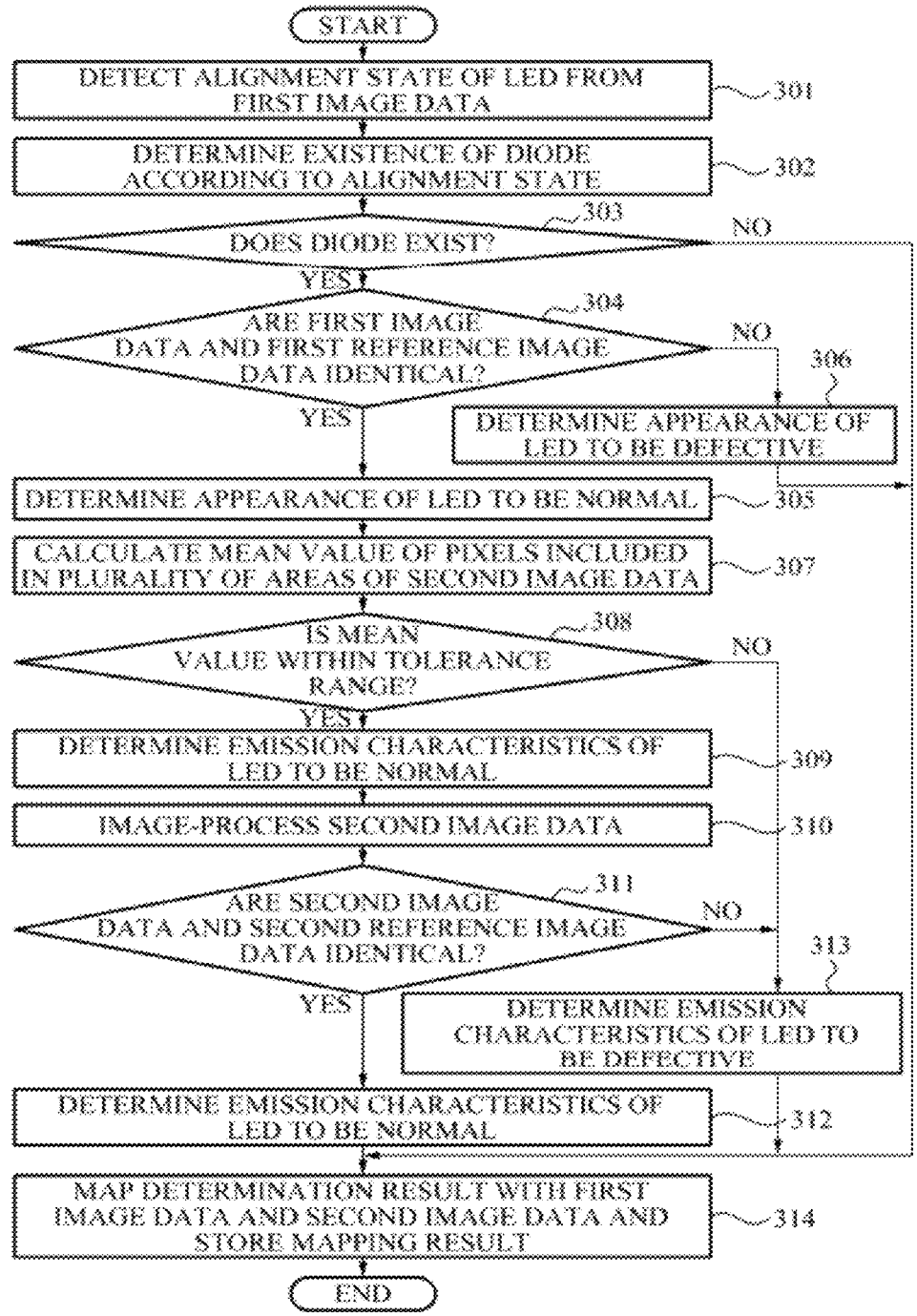
FIG. 3 is a flowchart illustrating a method of determining a defect in appearance and emission characteristics of an LED, according to an embodiment of the present invention.

FIG. 3 is a flowchart illustrating a method of determining the defect in appearance and emission characteristics of an LED, according to an embodiment of the present invention. FIG. 3 illustrates operation 250 of FIG. 2 in detail.

The LED inspection apparatus 100 may determine the defect in the appearance of the LED 110 using the first image data, and the defect in the emission characteristics using the second image data.

That is, the LED inspection apparatus 100 may detect an alignment state of the LED 110 from the first image data in operation 301, and determine an existence of a diode according to the detected alignment state in operation 302. When the alignment state has a discontinuous section or an undetectable section in the first image data, the LED inspection apparatus 100 may determine that the diode is absent.

When the first image data is determined to include the diode in operation 303, the LED inspection apparatus 100 may determine whether the first image data is identical to the first reference image data in operation 304. That is, the LED inspection apparatus 100 may compare a border of the first image data and a reference border of the first reference image data, thereby determining whether the two borders are identical. Alternatively, the LED inspection apparatus 100 may compare pixel values of the first image data with reference pixel values of the first reference image data, thereby determining whether two corresponding pixel values are identical or whether a difference is within a tolerance range.

When the first image data is identical to the first reference image data, the LED inspection apparatus 100 may determine that the LED 110 has a normal appearance in operation 305. When the first image data is different from the first reference image data, the LED inspection apparatus 100 may determine that the LED 110 has a defective appearance operation 306. In this case, for example, the LED 110 may have damage such as breakage or may be contaminated.

When the LED 110 is determined to have the normal appearance, the LED inspection apparatus 100 may calculate a mean value of pixels included in a plurality of areas of the second image data in operation 307.

Next, the LED inspection apparatus 100 may check whether the mean value is within a tolerance range in operation 308. The LED inspection apparatus 100 may determine that the LED 110 has normal emission characteristics when the mean value is within the tolerance range in operation 309, or defective emission characteristics when the mean value is beyond the tolerance range in operation 313.

When the LED 110 is determined to have the normal emission characteristics in operation 309, the LED inspection apparatus 100 may image-process the second image data in operation 310. The image-processing is performed to secondly determine the defect in the emission characteristics of the LED 110 using the image-processed second image data.

The LED inspection apparatus 100 may determine whether the image-processed second image data is identical to the second reference image data or whether a difference is within a tolerance range, in operation 311. Specifically, for this purpose, pixels included in the second image data may be compared with pixels included in the second reference image data.

When the image-processed second image data is identical to the second reference image data, the LED inspection apparatus 100 may determine that the LED 110 has the normal emission characteristics in operation 312. When the image-processed second image data is different from the second reference image data, the LED inspection apparatus 100 may determine that the LED 110 has the defective emission characteristics in operation 313.

The LED inspection apparatus 100 may map the determination result with the first image data and the second image data and store the mapping result, in operation 314. That is, the LED inspection apparatus 100 may generate determination result data.

Figure 4:
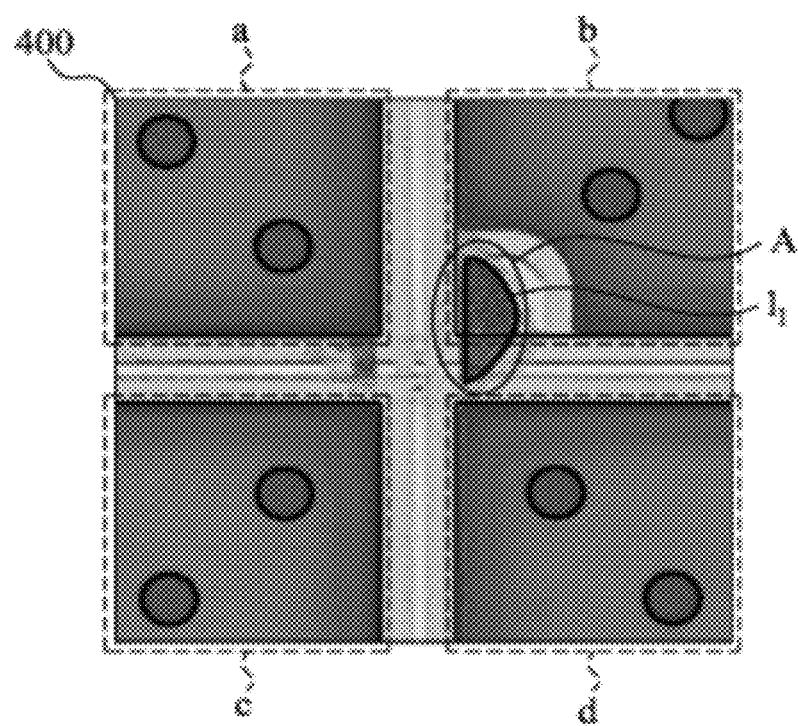
FIGS. 4 and 5 are diagrams illustrating first image data and second image data according to an embodiment of the present invention.
Figure 5:
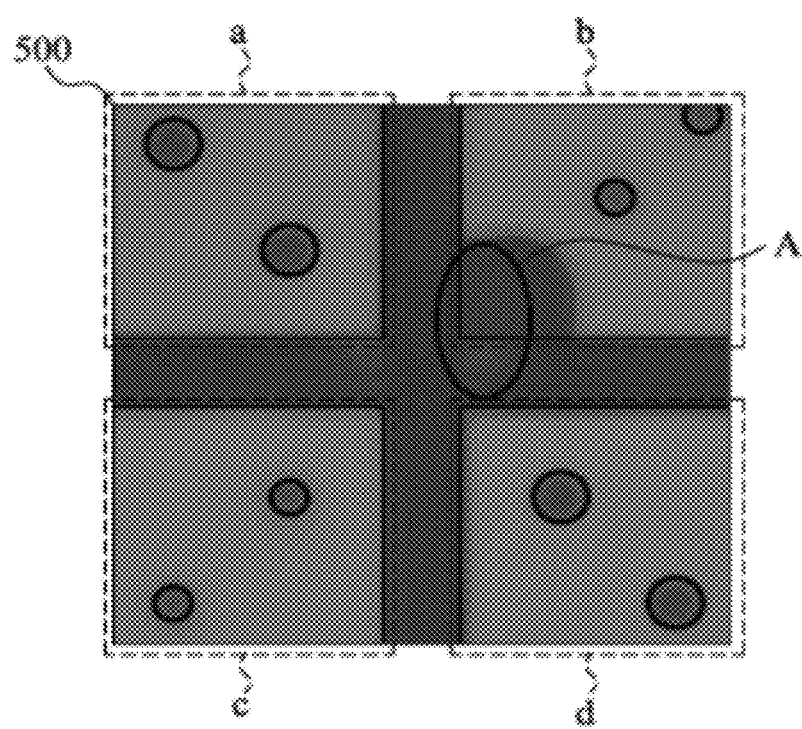

FIGS. 4 and 5 are diagrams illustrating first image data and second image data according to an embodiment of the present invention. FIG. 4 shows first image data 400 photographed by emitting visible light to a plurality of LEDs. FIG. 5 shows second image data 500 photographed by emitting UV light to the same LEDs.

Referring to FIG. 4, the first image data 400 includes first to fourth diode areas a, b, c, and d. A border of the first image data 400 is detected in the first to fourth diode areas a, b, c, and d. Therefore, it is recognized that an area A of the second diode area b is damaged. During border detection of the first image data 400, a border $I_1$ may also be detected from a damaged area included in the area A.

First reference image data (not shown) does not include the border included in the area A. That is, the first image data 400 is not identical to the first reference image data. Accordingly, the LED corresponding to the first image data 400 may be determined to have a defective appearance.

Referring to FIG. 5, the second image data 500 includes first to fourth diode areas a, b, c, and d, in the same manner as the first image data 400. The first to fourth diode areas a, b, c, and d may include pixel values corresponding to light generated from an active layer of the LED and light of which a wavelength is converted by a phosphor.

For example, when blue light is generated from the active layer of the LED while the phosphor wavelength-converts the blue light to yellow light, the pixels included in first to fourth diode areas a, b, c, and d may have a pixel value corresponding to mixture of the blue light and the yellow light. Therefore, when the LED has the normal emission characteristics, the mean value of the pixels included in the first to fourth diode areas a, b, c, and d may be within a tolerance range.

The first diode area a among the first to fourth diode areas a, b, c, and d may include almost no pixel values corresponding to the blue light but include pixel values corresponding to yellow light. Therefore, the mean value of the pixels of the first diode area a may be beyond the tolerance range. That is, the LED has defective emission characteristics and does not normally generate blue light.

As shown in FIGS. 4 and 5, the damaged area included in the area A is not detected from the second image data 500 due to the wavelength-converted light. Therefore, the appearance defect of the LED may be inspected using the first image data 400 which is an image of the visible light.

Also, the emission characteristics related to the first diode area a is not inspected with the first image data 400 since the first image data 400 has no luminance change by the wavelength-converted light. Accordingly, the defect in the emission characteristics may be inspected using the second image data 500 which is an image of the UV light.

Figure 6:
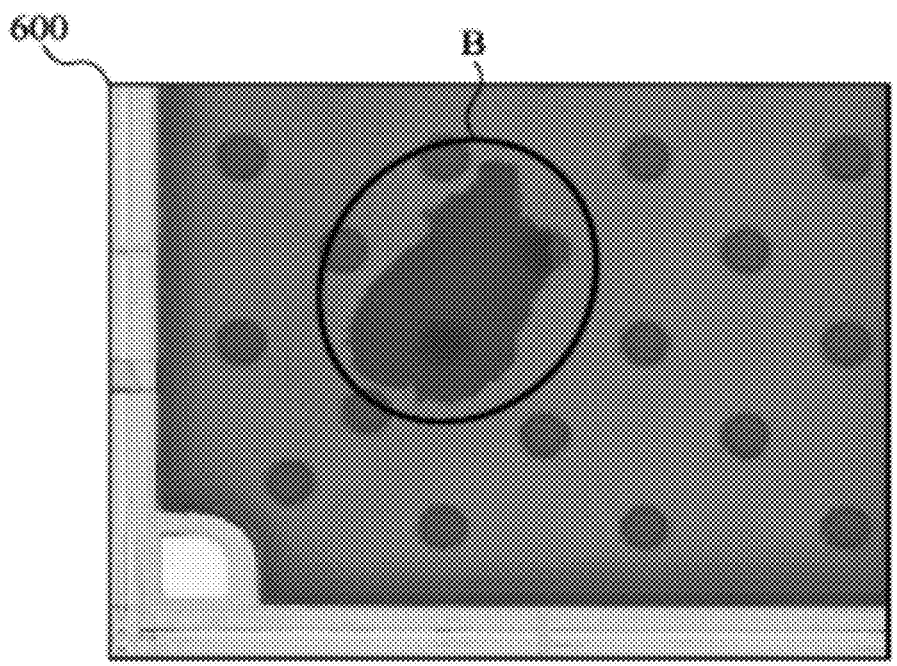
FIGS. 6 and 7 are diagrams illustrating first image data and second image data according to another embodiment of the present invention.
Figure 7:
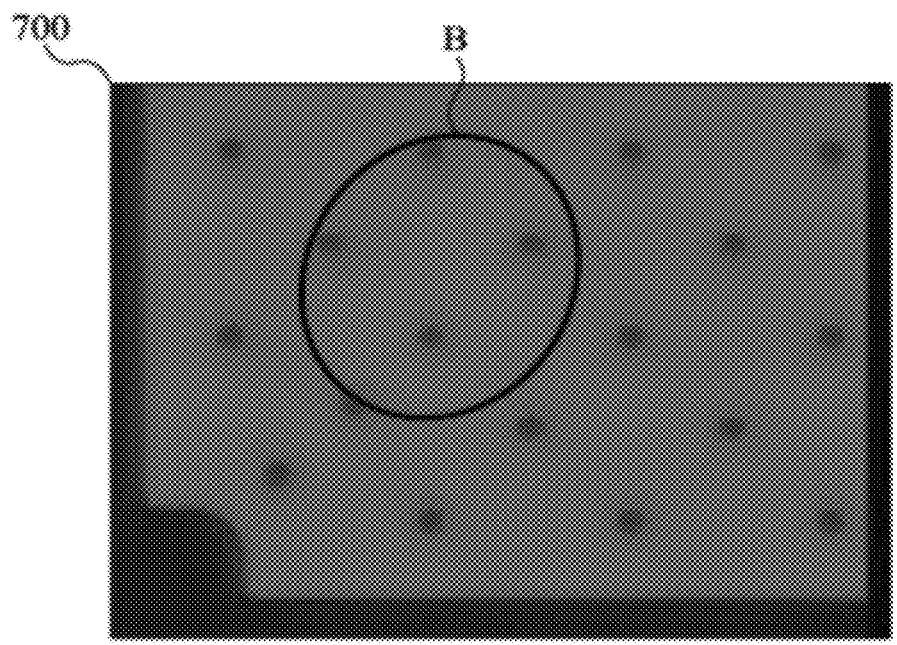

FIGS. 6 and 7 are diagrams illustrating first image data and second image data according to another embodiment of the present invention. The first image data shown in FIG. 6 is photographed by emitting visible light to an LED. The second image data shown in FIG. 7 is photographed by emitting UV light to the same LED.

Referring to the first image data 600 shown in FIG. 6, a defect in appearance is inspected in an area B. Pixel values of the first image data 600 and first reference image data (not shown) do not correspond to each other in the area B. Therefore, the LED corresponding to the first image data 600 may be determined to be contaminated.

The second image data 700 shown in FIG. 7 is an image of the LED of which the area B is contaminated. However, a defect in emission characteristics included in the area B is not detected due to an influence of wavelength-converted light. Therefore, the defect in the appearance may be inspected using the first image data 600 which is an image of the visible light.

Figure 8:
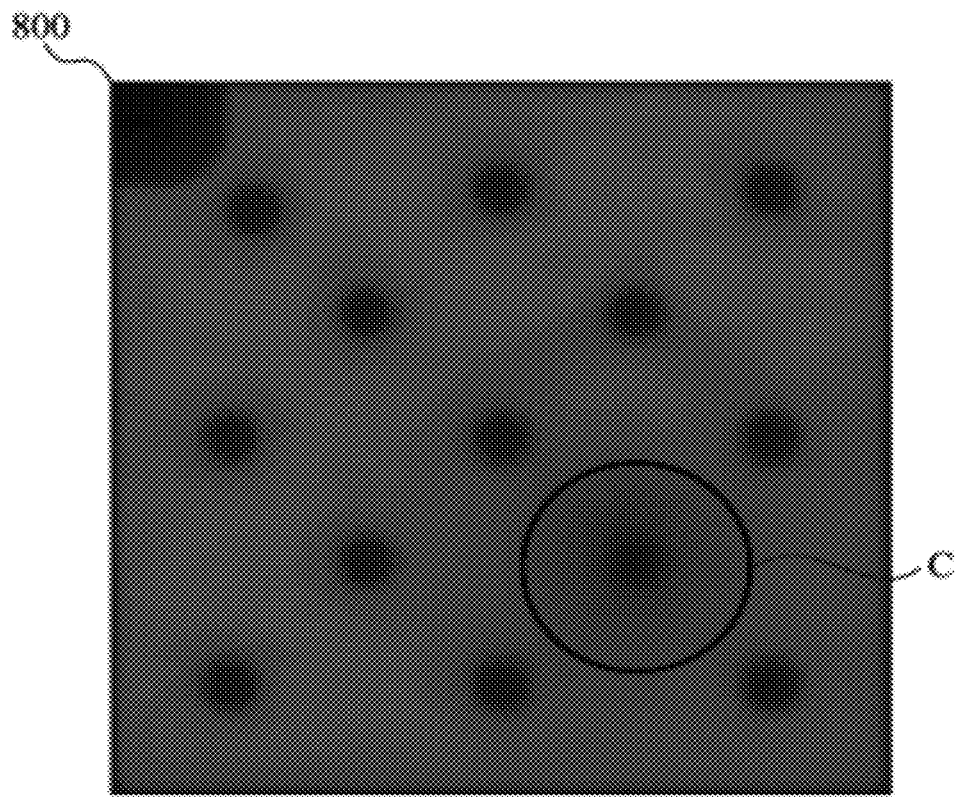
FIGS. 8 and 9 are diagrams illustrating second image data and image-processed second image data according to an embodiment of the present invention.
Figure 9:
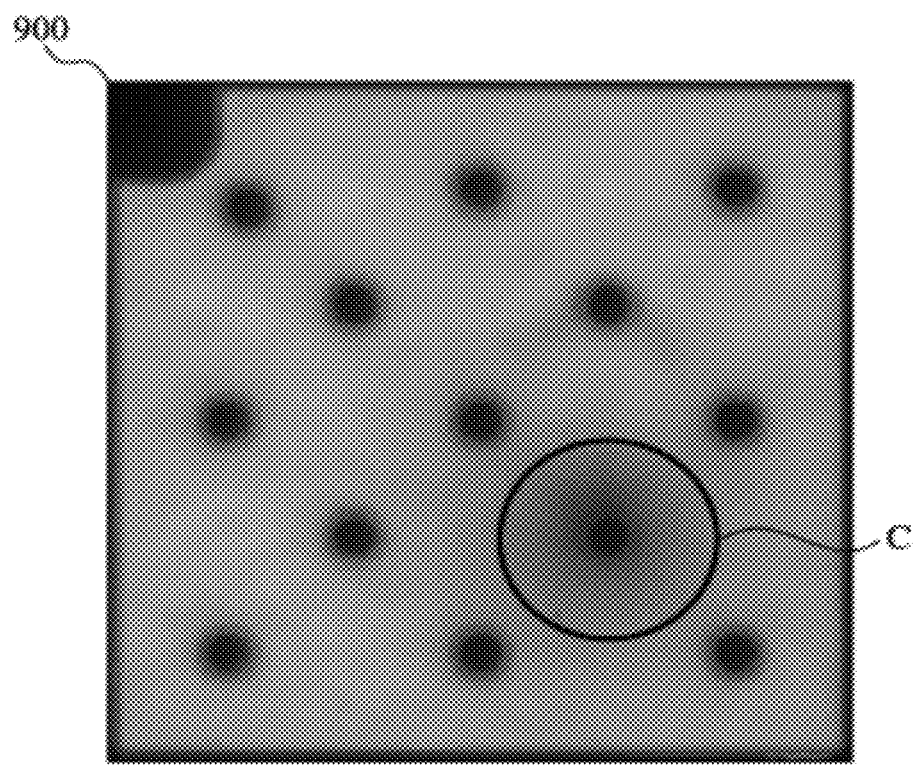

FIGS. 8 and 9 are diagrams illustrating second image data and image-processed second image data according to an embodiment of the present invention. In the second image data shown in FIG. 8, the emission characteristics of the LED are inspected using wavelength-converted light. Therefore, a minor dot or spot may not be accurately inspected due to the wavelength-converted light. Therefore, an LED inspection apparatus may image-process the second image data into a black-and-white image.

FIG. 8 shows the second image data 800 photographed by emitting UV light to LEDs. FIG. 9 shows image-processed image data 900 image-processed from the image data 800 of FIG. 8.

Referring to FIGS. 8 and 9, the second image data 800 and the image-processed second image data 900 include a spot in an area C. The spot is related to the emission characteristics of the LED. However, since the inspection may not be accurately performed using the second image data 800, the image-processed second image data 900 may be used for the inspection.

Figure 10:
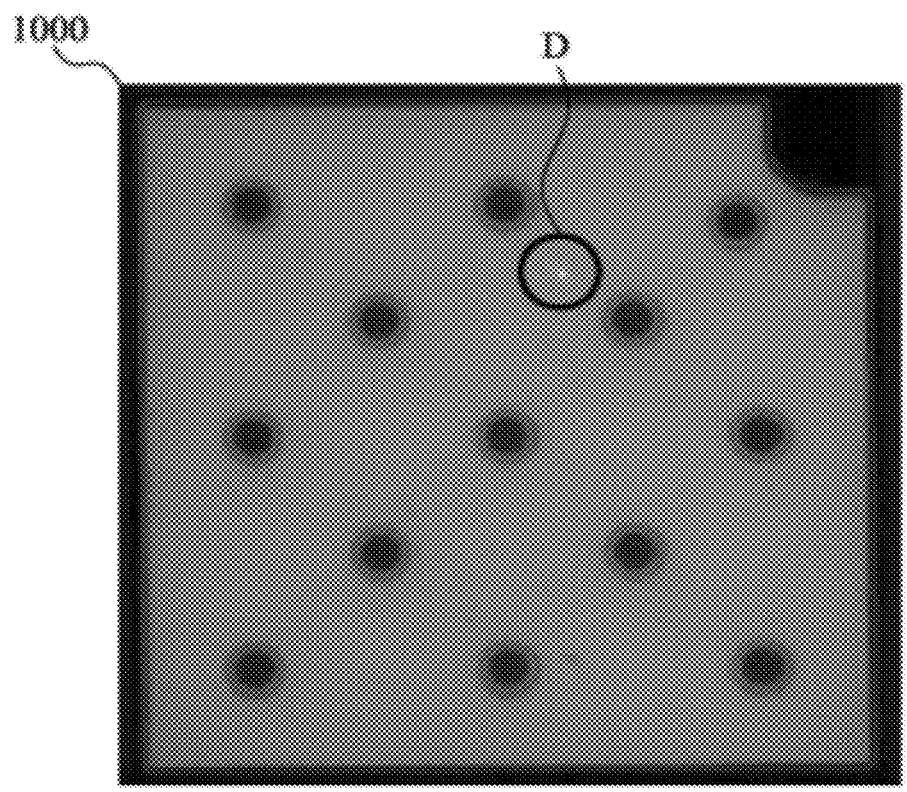
FIGS. 10 to 12 are diagrams illustrating image-processed second image data according to other embodiments of the present invention.
Figure 11:
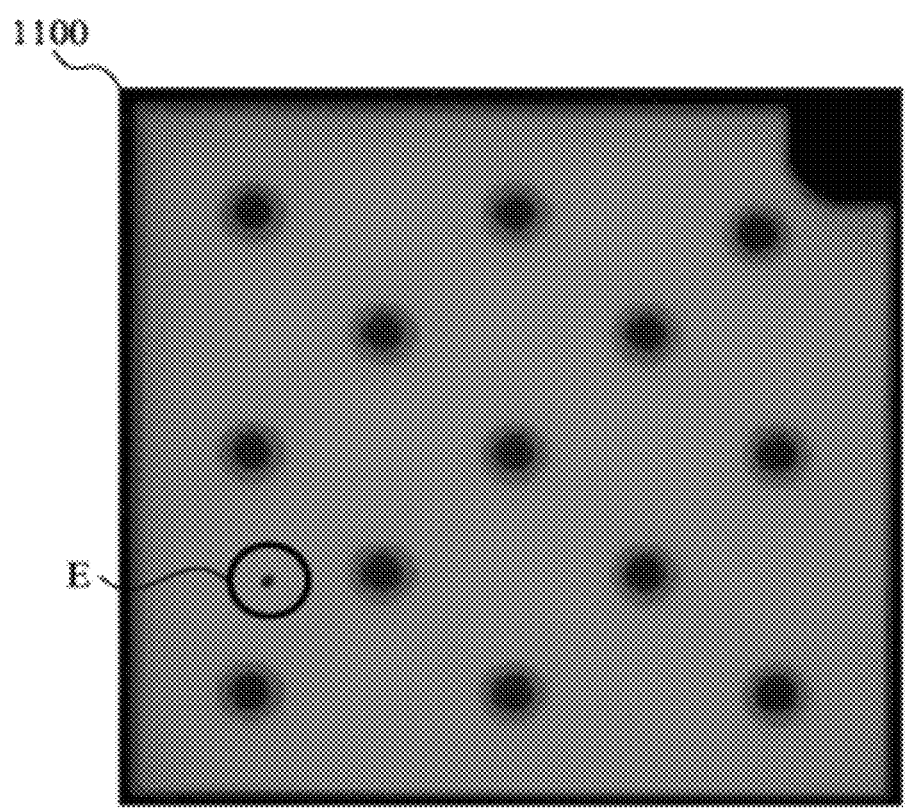
Figure 12:
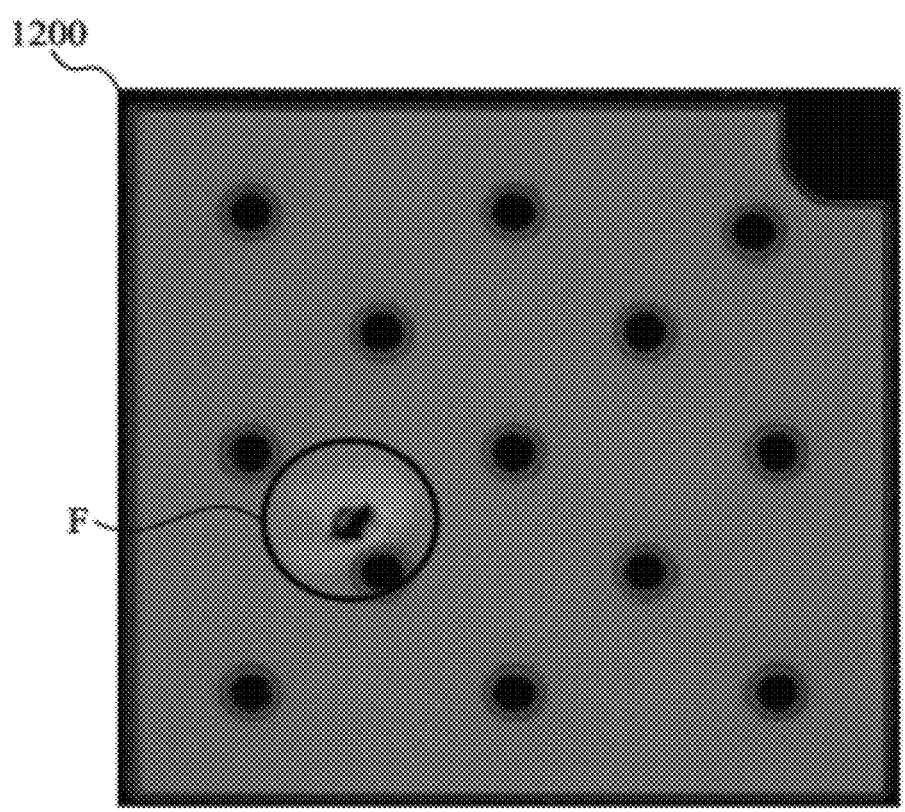

FIGS. 10 to 12 are diagrams illustrating image-processed second image data according to other embodiments of the present invention. FIGS. 10 to 12 are image-processed second image data 1000, 1100, and 1200 obtained by photographing LEDs including respectively different defects of emission characteristics.

Second image data 1000 shown in FIG. 10 includes a white spot in an area D. Second image data 1100 shown in FIG. 11 includes a dark spot in an area E. Second image data 1200 shown in FIG. 12 includes a white spot and a dark spot in an area F.

The white spot is caused by a pattern defect of the LED. The dark spot may be caused by a crack occurring in a semiconductor layer, in particular, a gallium-nitride (GaN) semiconductor layer. An energy bond in an active layer of the LED may not be normally achieved due to such defects, consequently leading to the white spot or the dark spot occurring. Since the white spot and the dark spot are not inspected through an visual inspection, the image-processed second image data may be used for the inspection.

The LED inspection apparatus and method according to the embodiments of the present invention determine a defect by inspecting appearance and emission characteristics simultaneously, thereby simplifying the inspection process.

The LED inspection apparatus and method according to the embodiments of the present invention use a UV LED as an inspection light source. Accordingly, the appearance and the emission characteristics may be inspected at a high speed.

Although a few exemplary embodiments of the present invention have been shown and described, the present invention is not limited to the described exemplary embodiments.

Instead, it would be appreciated by those skilled in the art that changes may be made to these exemplary embodiments without departing from the principles and spirit of the invention, the scope of which is defined by the claims and their equivalents.

What is claimed is:

1. A light emitting diode (LED) inspection apparatus comprising: at least one LED comprising a phosphor applied on an emission surface; a first lighting unit to emit visible light to the LED; a second lighting unit to emit ultraviolet (UV) light to the LED; a photographing unit to generate at least one first image data by photographing the visible light reflected from the LED and to generate at least one second image data by photographing the UV light reflected from the LED; and a determination unit to determine a defect in appearance and emission characteristics of the LED using the at least one first image data and second image data, and a determination unit to determine a defect in appearance and emission characteristics of the LED using the at least one first image data and second image data, wherein the determination unit divides the second image data into a plurality of sections and calculates a mean value of pixels comprised in the plurality of sections when the LED is determined to have a normal appearance, and determines that the LED has defective emission characteristics when the mean value is beyond a tolerance range.

2. The LED inspection apparatus of claim 1, further comprising a beam splitting unit to reflect the emitted visible light and transmit the reflected visible light to the LED, and to provide the visible light reflected from the LED to the photographing unit by transmitting the visible light.

3. The LED inspection apparatus of claim 1, wherein the UV light reflected from the LED comprises a wavelength-converted light of which a wavelength is converted by the LED and the phosphor.

4. The LED inspection apparatus of claim 3, further comprising a color filter disposed at an upper portion of the LED to pass the wavelength-converted light which is comprised in the UV light reflected from the LED and to filter the UV light.

5. The LED inspection apparatus of claim 4, wherein the photographing unit generates second image data by photographing the wavelength-converted light passed through the color filter.

6. The LED inspection apparatus of claim 1, wherein the determination unit detects an alignment state of the LED from the first image data and determines an existence of a diode according to the alignment state.

7. The LED inspection apparatus of claim 6, wherein the determination unit compares the first image data with first reference image data when the diode is determined to exist, and determines that the LED has a defective appearance when the first image data is different from the first reference image data.

8. The LED inspection apparatus of claim 1, wherein the determination unit image-processes the second image data when the mean value is within the tolerance range, and compares the second image data with second reference image data and determines that the LED has defective emission characteristics when the second image data is different from the second reference image data.

9. The LED inspection apparatus of claim 1, further comprising:
a display unit to display the first image data and the second image data generated by the photographing unit; and
a storage unit to map the first image data and the second image data with a result of the determination by the determination unit related to the defect in appearance and emission characteristics, and store the mapping result.

10. A light emitting diode (LED) inspection method emitting visible light to at least one LED which comprises a phosphor applied on an emission surface generating at least one first image data by photographing the visible light reflected from the LED emitting ultraviolet (UV) light to the LED generating at least one second image data by photographing the UV light reflected from the LED and determining a defect in appearance and emission characteristics of the LED using the first image data and the second image data) A light emitting diode (LED) inspection method comprising: emitting visible light to at least one LED which comprises a phosphor applied on an emission surface; generating at least one first image data by photographing the visible light reflected from the LED; emitting ultraviolet (UV) light to the LED; generating at least one second image data by photographing the UV light reflected from the LED; and determining a defect in appearance and emission characteristics of the LED using the first image data and the second image data, wherein the determining of the defect comprises: dividing the second image data into a plurality of sections and calculating a mean value of pixels comprised in the plurality of sections when the LED is determined to have a normal appearance; and determining that the LED has defective emission characteristics when the mean value is beyond a tolerance range.

11. The LED inspection method of claim 10, wherein the UV light reflected from the LED comprises a wavelength-converted light of which a wavelength is converted by the LED and the phosphor.

12. The LED inspection method of claim 10, wherein the generating of the second image data comprises:
passing the wavelength-converted light which is comprised in the UV light reflected from the LED and filtering the UV light; and
generating the second image data by photographing the filtered wavelength-converted light.

13. The LED inspection method of claim 10, wherein the determining of the defect comprises:
detecting an alignment state of the LED from the first image data and determining an existence of a diode according to the alignment state;
comparing the first image data with first reference image data when the diode is determined to exist; and
determining that the LED has a defective appearance when the first image data is different from the first reference image data.

14. The LED inspection method of claim 10, wherein the determining of the defect comprises: image-processing the second image data when the mean value is within the tolerance range; and comparing the second image data with second reference image data and determining that the LED has defective emission characteristics when the second image data is different from the second reference image data.

15. The LED inspection method of claim 10, further comprising:
displaying the first image data and the second image data; and
mapping the first image data and the second image data with a result of the determination related to defects in appearance and emission characteristics and storing the mapping result.

* * * * *